(12) United States Patent
Kasprzak et al.

(10) Patent No.: US 9,149,372 B2
(45) Date of Patent: Oct. 6, 2015

(54) STENT GRAFT ADAPTOR

(71) Applicant: Cook Medical Technologies LLC, Bloomington, IN (US)

(72) Inventors: Piotr Miroslaw Kasprzak, Regensburg (DE); Werner Dieter Ducke, Eight Mile Plains (AU); David Ernest Hartley, Wannanup (AU); Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/798,532

(22) Filed: Mar. 13, 2013

(65) Prior Publication Data
US 2013/0297001 A1   Nov. 7, 2013

(30) Foreign Application Priority Data

May 2, 2012   (AU) .................................. 2012202565

(51) Int. Cl.
 *A61F 2/06* (2013.01)
 *A61F 2/848* (2013.01)
 *A61F 2/07* (2013.01)
 *A61F 2/966* (2013.01)
 *A61F 2/95* (2013.01)
 *A61F 2/89* (2013.01)

(52) U.S. Cl.
 CPC . *A61F 2/848* (2013.01); *A61F 2/07* (2013.01); *A61F 2/966* (2013.01); *A61F 2/89* (2013.01); *A61F 2002/061* (2013.01); *A61F 2002/077* (2013.01); *A61F 2002/9511* (2013.01); *A61F 2250/006* (2013.01)

(58) Field of Classification Search
 CPC ..... A61F 2/848; A61F 2/07; A61F 2002/075; A61F 2/966; A61F 2/89; A61F 2002/061; A61F 2002/077; A61F 2250/006; A61F 2002/9511
 USPC ........................................ 623/1.12, 1.13, 1.14
 See application file for complete search history.

(56) References Cited

U.S. PATENT DOCUMENTS

| | | | |
|---|---|---|---|
| 4,728,328 A * | 3/1988 | Hughes et al. | 623/23.69 |
| 6,451,050 B1 | 9/2002 | Rudakov et al. | |
| 7,766,959 B2 | 8/2010 | DiMatteo et al. | |
| 2002/0052643 A1 | 5/2002 | Wholey et al. | |
| 2003/0236567 A1 * | 12/2003 | Elliot | 623/1.13 |
| 2006/0217796 A1 | 9/2006 | DiMatteo et al. | |
| 2008/0288044 A1 * | 11/2008 | Osborne | 623/1.13 |
| 2010/0256754 A1 | 10/2010 | Styrc | |
| 2011/0029059 A1 * | 2/2011 | Christiansen et al. | 623/1.2 |

FOREIGN PATENT DOCUMENTS

WO   03053283 A1   7/2003

* cited by examiner

Primary Examiner — Tuan V Nguyen
Assistant Examiner — Tin Nguyen
(74) Attorney, Agent, or Firm — Richard J. Godlewski (57) ABSTRACT

A stent graft adaptor has an outer graft tube and an inner graft tube with the inner graft tube substantially concentric with and within the outer graft tube. A joining member extends between the inner tube and the outer tube. The joining member can be a continuous fold of graft material extending from a proximal end of the outer tube to a proximal end of the inner tube. The inner tube has at least one self expanding stent on an outer surface thereof and the outer graft tube has at least one self expanding stent on an inner surface. The outer surface of the outer tube provides a sealing surface to engage against the wall of a vessel and the inner tube provides a sealing surface to engage with a corresponding sealing surface of a stent graft deployed through it. The outer sealing surface can include barbs.

19 Claims, 6 Drawing Sheets

STENT GRAFT ADAPTOR

TECHNICAL FIELD

This invention relates to a medical device and more particularly to a medical device for introduction by endovascular techniques.

BACKGROUND OF THE INVENTION

Stent grafts are used for endovascular introduction into the vasculature of a patient. Generally these stent grafts are used to bridge a defect or damaged portion of the vasculature by providing an alternate flow path. Generally the stent graft is placed so that its ends engage on to non-diseased vasculature either side of the damaged portion. Where there are branch vessels extending from the vasculature, side branches can be provided but a side vessel is very small it is usually not practical to provide a side branch.

In one particular situation when stent grafts are placed into the thoracic region of the aorta, there may be occluded one or more intercostal arteries either because a stent graft has a landing zone where there is an intercostal artery or the intercostal artery exists in the damaged area.

Occlusion of intercostal arteries can cause temporary or permanent paraplegia and it is an object of this invention to alleviate or prevent the risk of such paraplegia.

DISCLOSURE OF THE INVENTION

In one form therefore, although this may not necessarily be the broadest or only form, the invention is said to reside in a stent graft adaptor comprising an outer graft tube and an inner graft tube, the outer graft tube being substantially concentric with the inner graft tube, the outer graft tube and the inner graft tube defining an annular region therebetween and a joining member extending between the inner graft tube and the outer graft tube and the joining member closing off the annular region to prevent fluid flow through the annular region.

Preferably an outer surface of the outer graft tube comprises a sealing surface to engage against the wall of a vessel and the inner tube comprises a sealing surface to engage with a corresponding sealing surface of a stent graft deployed therethrough.

Preferably the inner graft tube comprises at least one self expanding stent on an outer surface thereof and the outer graft tube comprises at least one self expanding stent on an inner surface thereof.

Preferably the joining member comprises a continuous fold of graft material extending from a first end of the outer tube to a first end of the inner tube.

Alternatively the joining member can comprise an annular portion of graft material fastened to and extending from an inner surface of the outer graft tube to and fastened to an outer surface of the inner graft tube. In such a situation the annular portion of graft material can extend between the outer tube and the inner tube at a location between the ends of the outer tube and the inner tube.

Preferably the stent graft adaptor comprises barbs extending outwards from the outer graft tube in use to engage with the wall of a vessel into which the adaptor is deployed.

Preferably the outer graft tube comprises a diameter of up to 46 mm to fit in most descending aortas and the inner graft tube comprises a diameter of 32 mm to mate with an interference fit into a 34 mm thoracoabdominal device and the outer graft tube comprises a length of about 50 mm.

In an alternate form the invention comprises a stent graft adaptor comprising an outer graft tube and an inner graft tube, the outer graft tube being substantially concentric with the inner graft tube, the outer graft tube and the inner graft tube defining an annular region therebetween and a joining member extending between the inner graft tube and the outer graft tube and the joining member closing off the annular region to prevent fluid flow through the annular region, the joining member comprising a continuous fold of graft material extending from a proximal end of the outer tube to a proximal end of the inner tube, the inner graft tube comprising at least one self expanding stent on an outer surface thereof and the outer graft tube comprising at least one self expanding stent on an inner surface thereof, whereby an outer surface of the outer graft tube provides a sealing surface to engage against the wall of a vessel and the inner tube provides a sealing surface to engage with a corresponding sealing surface of a stent graft deployed therethrough.

In an alternate form the invention comprises a stent graft adaptor in combination with an introducer, the introducer comprising a pusher, the pusher comprising a proximal end to be introduced into a patient and a distal end, a dilator at the proximal end of the pusher, a first temporary retention arrangement on the pusher distal of the dilator, the stent graft adaptor comprising an outer graft tube and an inner graft tube, the outer graft tube being substantially concentric with the inner graft tube, the inner graft tube having a first diameter and a proximal end and a distal end, the outer graft tube having a second diameter and a proximal end and a distal end, the first diameter being smaller than the second diameter, a joining member extending between the proximal end of the inner graft tube and the proximal end of the outer graft tube, the inner graft tube comprises one self expanding stent on an outer surface thereof and the outer graft tube comprises at least one self expanding stent on an inner surface thereof, the stent on the inner graft tube being at a distal end of the inner graft tube, the stent graft adaptor being mounted onto the introducer with the distal end of the inner tube and the stent of the inner tube retained distally of the dilator by the first temporary retention arrangement an the joining member and the outer graft tube distally thereof.

Preferably the stent graft adaptor in combination with an introducer further includes a second temporary retention arrangement distal of the first retention arrangement, the distal end of the outer tube being temporarily retained by the second temporary retention arrangement.

Preferably the stent graft adaptor in combination with an introducer further comprises barbs extending outwards from the outer graft tube in use to engage with the wall of a vessel into which the adaptor is deployed.

It will be seen that by this invention there is provided an arrangement which can act as an adaptor for placement of a stent graft and which reduces the amount of landing zone necessary which can potentially give a reduction in the potential for temporary or permanent paraplegia.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

Various stent types and stent constructions may be used in the stent graft of the present invention. In general, the stents may be formed from any material and have any structure that is expandable and has sufficient radial strength to retain its shape. For example, the stents may be balloon expandable or self-expanding stents. The stents may be capable of radially contracting, radially distensible and/or deformable. Self-expanding stents include those that have a spring-like action which causes the stent to radially expand, or stents which expand due to the memory properties of the stent material for a particular configuration at a certain temperature. A preferred self-expanding stent is the Z-STENT®, available from Cook, Incorporated, Bloomington, Ind. USA.

Any suitable stent material is contemplated including, but not limited to, stainless steel, platinum, gold, titanium, Nitinol™ and other nickel-titanium alloys, MP35N® and other nickel-cobalt alloys, Cobalt L-605™ and other cobalt-chromium alloys, other biocompatible metals, metal-alloys, as well as polymeric stents.

This then generally describes the invention but to assist with understanding reference will now be made to the accompanying drawings which show preferred embodiments of the invention.

DESCRIPTION OF PREFERRED EMBODIMENTS

Figure 1A:
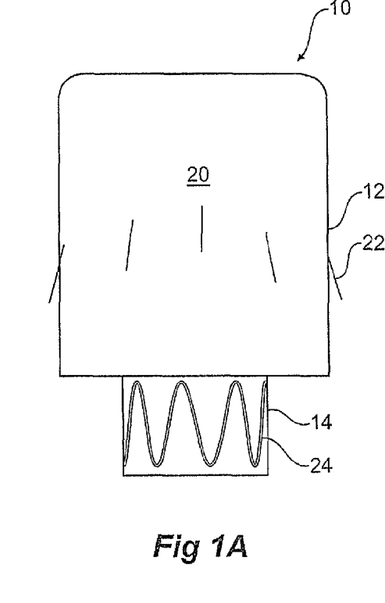
FIGS. 1A and 1B show a first embodiment of stent graft adaptor according to the present invention.
Figure 1B:
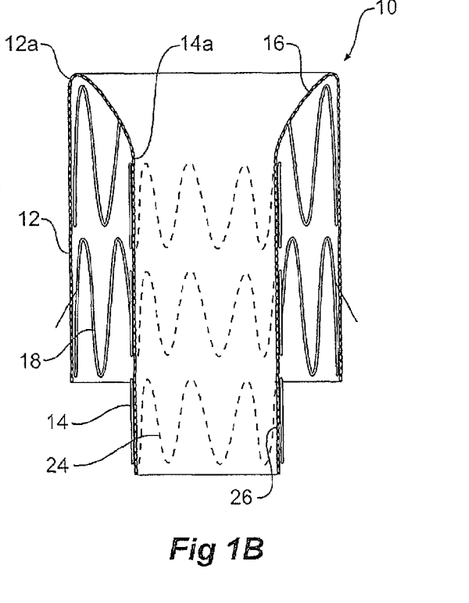

Now looking at the drawings and in particular FIGS. 1A and 1B, it will be seen that a stent graft adaptor 10 according to one embodiment of the invention comprises an outer graft tube 12 and an inner graft tube 14. The inner graft tube 14 is substantially concentric with the outer graft tube and substantially within the outer graft tube. A connecting member 16 joins the outer graft tube from the top 12a of the outer graft tube to the top 14a of the inner graft tube. Preferably the inner graft tube 14, the outer graft tube 12 and the connecting member are formed from a single piece of biocompatible graft material.

The outer graft tube has at least one self-expanding zigzag stent 18 on its inner surface so that it presents an outer sealing surface 20. Barbs 22 fastened to the stent 18 extend out through the wall of the outer graft tube to engage in to the vasculature of a patient in use to prevent movement of the stent graft adaptor after it has been deployed into the vasculature.

The inner graft tube 14 has at least one and preferably a number of self-expanding stents 24 on its outer surface so that it presents an inner sealing surface 26. These self expanding stents can be relatively weak because all they need to do is to hold the inner tube open until a proximal end of a thoracoabdominal device or similar device is placed and expanded into it.

Figure 2A:
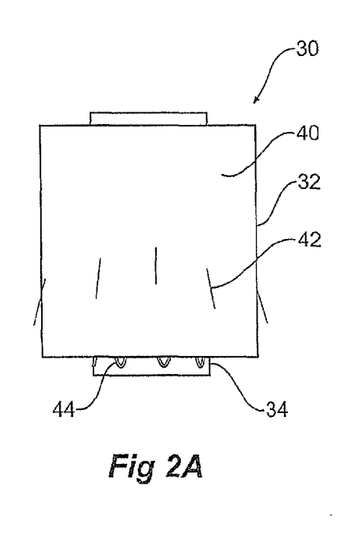
FIGS. 2A and 2B show an alternative embodiment of stent graft adaptor according to the present invention.
Figure 2B:
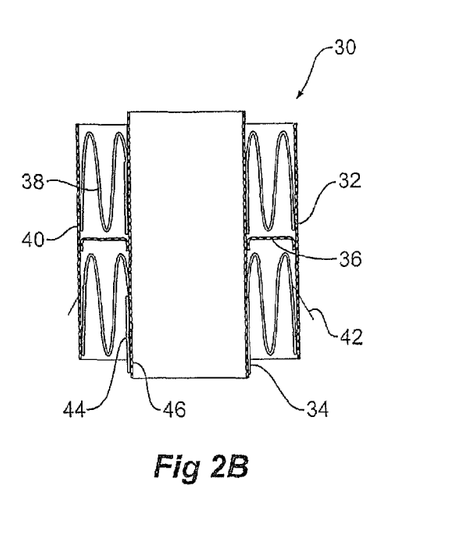

FIGS. 2A and 2B show an alternative embodiment of a stent graft adaptor 30 according to the present invention. In this embodiment the adaptor 30 has an outer tube 32 and an inner tube 34. The inner graft tube 34 is substantially concentric with the outer graft tube 32 and substantially within the outer graft tube 32. A connecting member 36 joins the outer graft tube with the inner graft tube. The connecting member is an annular portion of graft material fastened to and extending from an inner surface of the outer graft tube to and fastened to an outer surface of the inner graft tube. The connecting member 36 extends between the outer tube and the inner tube at a location between the ends of the outer tube and the inner tube.

The outer graft tube 32 has at least one self-expanding zigzag stent 38 on its inner surface so that it presents an outer sealing surface 40. Barbs 42 fastened to the stent 38 extend out through the wall of the outer graft tube to engage in to the vasculature of a patient in use to prevent movement of the stent graft adaptor after it has been deployed into the vasculature.

The inner graft tube 34 has at least one and preferably a number of self-expanding stents 44 on its outer surface so that it presents an inner sealing surface 46. These self expanding stents can be relatively weak because all they need to do is to hold the inner tube open until a proximal end of a thoracoabdominal device or similar device is placed and expanded into it.

The device as shown in either of FIGS. 1A and 1B or 2A and 2B is in use compressed onto an introducer device to be introduced into the vasculature of a patient. Generally the device of the present invention would be deployed first at a selected position in the vasculature to occlude as few as possible or none of the intercostal arteries and then a thoracoabdominal device deployed so that its proximal end is expanded or expands into the inner tube to provide a proximal seal for the thoracoabdominal device.

Figure 3:
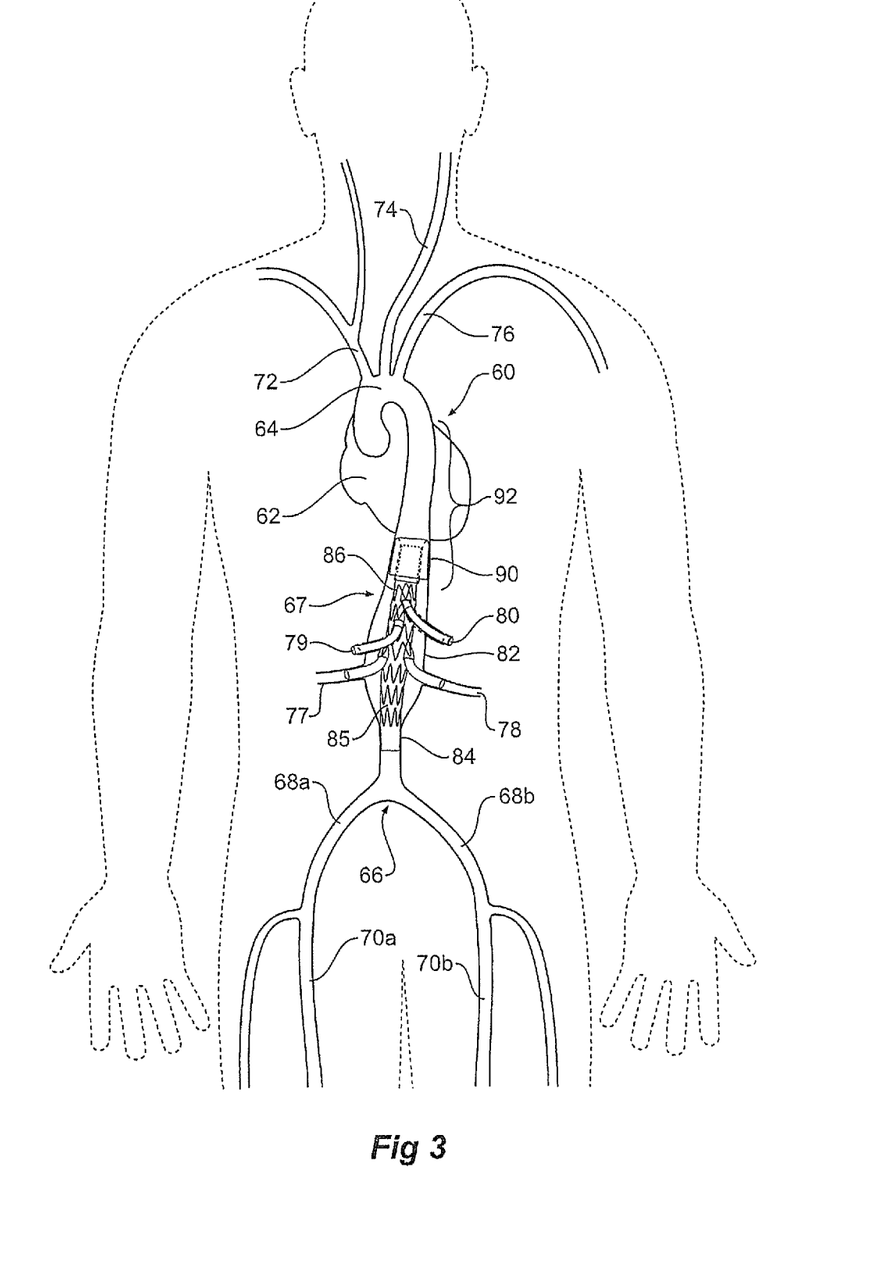
FIG. 3 shows the aortic vasculature of a patient including the placement of a thoracoabdominal stent graft and a stent graft adaptor according to the present invention.

FIG. 3 shows a schematic view of the aortic vasculature of a human body. The vasculature shown comprises an aorta 60 extending from a heart 62 over a thoracic arch 64 to an aortic bifurcation 66 via a descending aorta 67. At the aortic bifurcation iliac arteries 68a and 68b extend down to respective femoral arteries 70a and 70b. From the thoracic arch 64 the brachiocephalic artery 72, the left carotid artery 74 and the left subclavian artery 76. In the aorta there are renal arteries 77 and 78 and extending from the aorta a little above the renal arteries are the superior mesenteric artery 79 and the celiac artery 80. These four arteries can generally be referred to as the pararenal arteries. The aorta 60 is depicted with an aneurism 82 which has occurred in the region of the pararenal arteries and as illustrated, a stent graft has been deployed into the aorta with a distal landing zone 84 in a non-diseased part of the aorta adjacent to the aortic bifurcation 66 to seal the distal end of the stent graft 85. At the proximal end 86 of the stent graft 85 a stent graft adaptor 90 according to the present invention has been deployed.

Figure 4:
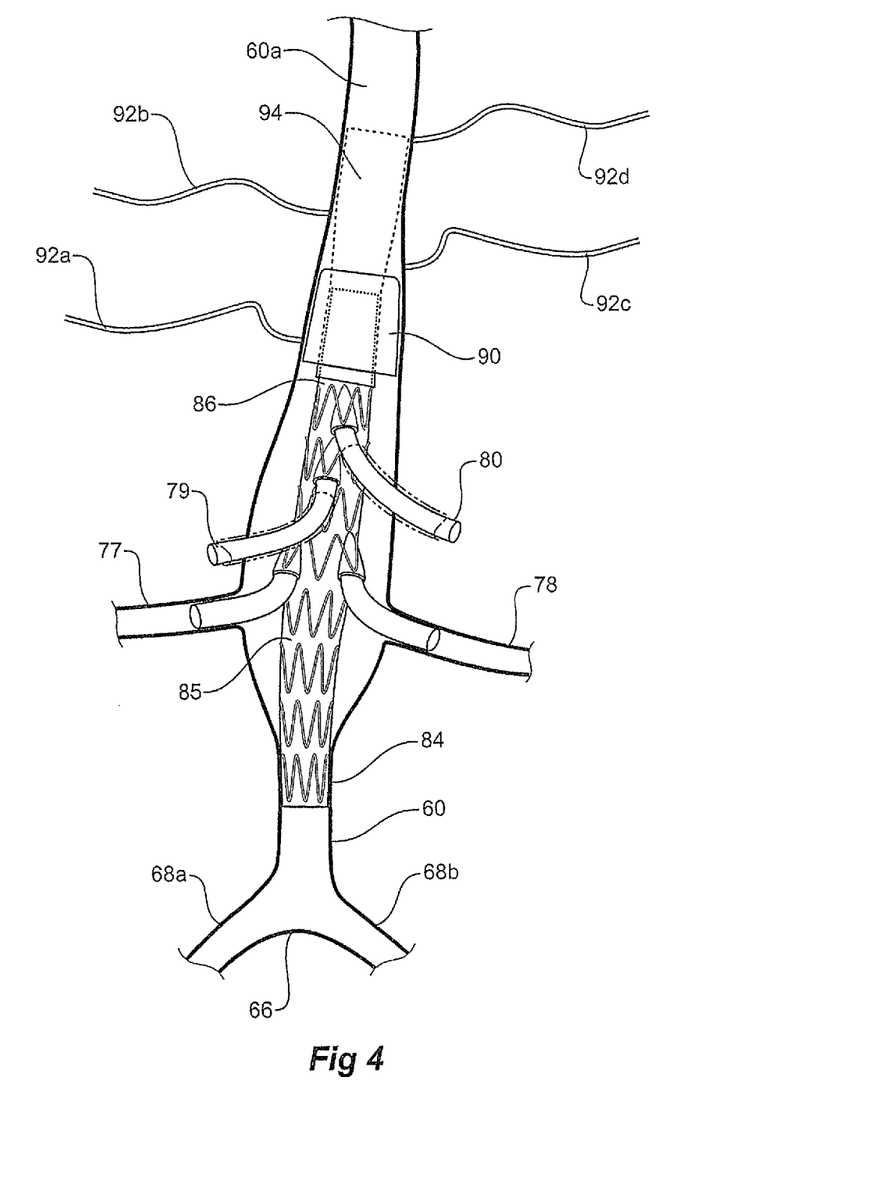
FIG. 4 shows detail of the thoracoabdominal vasculature as shown in FIG. 3.

The intercostal arteries which can cause problems with paraplegia are in the region indicated by the bracket 92 and as shown in more detail in FIG. 4.

FIG. 4 shows detail of the thoracoabdominal region shown in FIG. 3. The intercostal arteries in this region are shown as 92a to 92d.

It can be seen that the stent graft 85 has a diameter at its proximal end 86 of about 34 to 36 mm which is a smaller diameter than the diameter of the vasculature in this region and normally there would be placed a further stent graft extending further up the descending aorta 66. Such a stent graft is shown in part by the dotted lines 94.

As can be seen in FIG. 4 the placement of the adaptor 90 has caused occlusion of the intercostal artery 92a but not occlusion of the intercostal arteries 92b, 92c or 92d. If an alternative stent graft such as shown by the dotted lines 94 in FIG. 4 had been placed without essentially overlapping inner and outer tubes to act as an adaptor, then at least three intercostal arteries 92a, 92b and 92c would have been occluded and perhaps 92d as well depending on the size of the stent graft 94 and this would have considerably added to the risk of paraplegia.

Figures 5, 6, 7, 8:
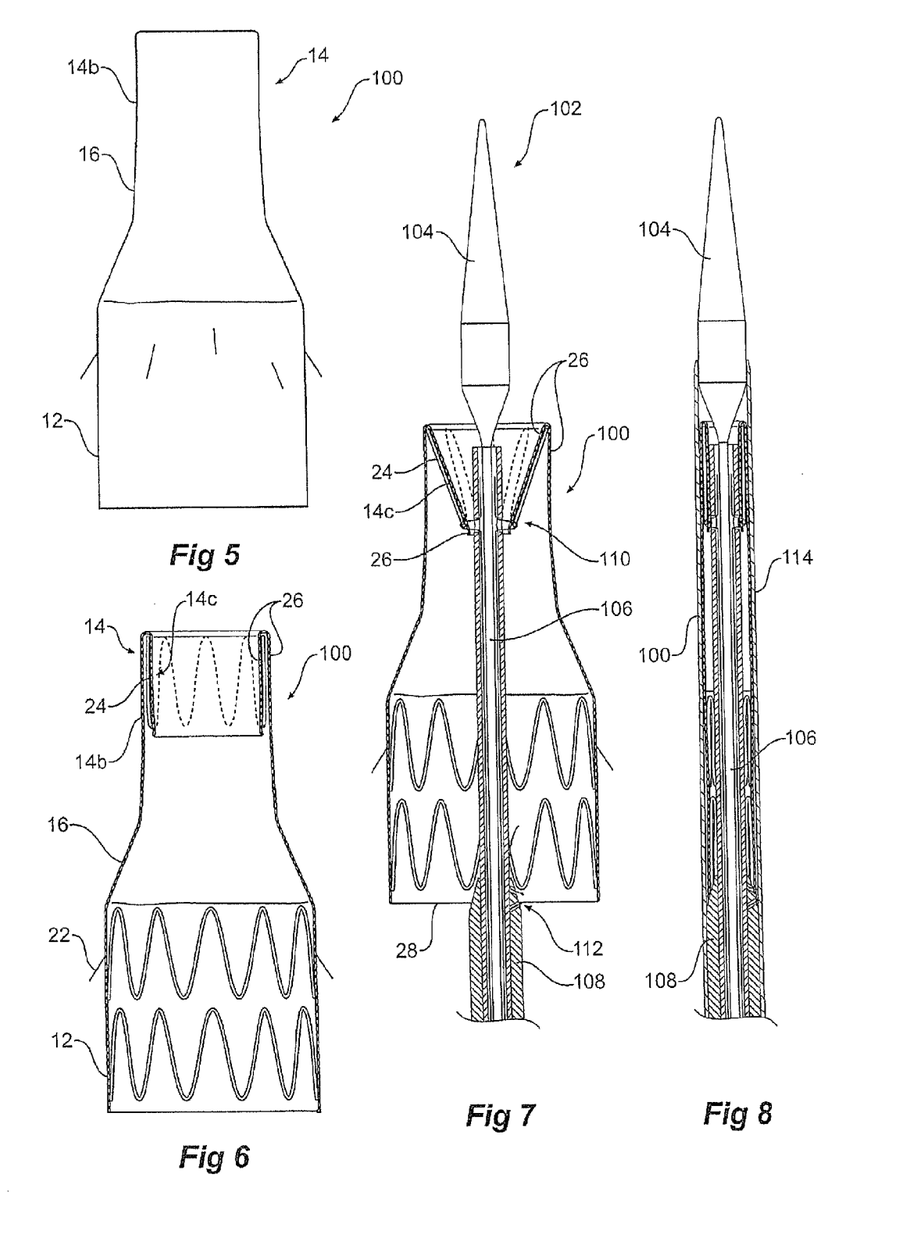
FIGS. 5 and 6 show views of an alternative embodiment of a stent graft adaptor according to the present invention in a configuration as it would be loaded on to a delivery device.
FIG. 7 shows the embodiment of FIGS. 5 and 6 loaded on to a delivery device.
FIG. 8 shows the device of FIGS. 5 and 6 loaded on to a delivery device and constrained for endovascular delivery.

FIGS. 5 and 6 show an alternative embodiment of a stent graft adaptor 100 of the present invention which is substantially the same as the embodiment shown in FIGS. 1A and 1B but is depicted in FIGS. 5 and 6 in a condition ready for mounting on an introducer device for deployment into the vasculature of a patient. In this embodiment the same reference numerals will be used as those in FIGS. 1A and 1B.

In the ready to deploy configuration shown in FIGS. 5 and 6 the stent graft adaptor 100 has an outer graft tube 12 is in substantially the same configuration as shown in FIGS. 1A and 1B but the connection member 16 extends away from the outer tube 12 and the inner tube 14 is partially inverted so that there is an outer portion 14b and an inner portion 14c of the inner tubular portion 14. The stents 18 on the outer tubular portion are in substantially the same positions as shown in FIGS. 1A and 1B but in this variation of the embodiment there is only one stent 24 on the inner tubular portion and in the ready to deploy condition this is mounted to the inner tubular portion 14c but between the inner tubular portion 14c and the outer tubular portion 14b. Hence when the stent graft adaptor 100 is finally deployed there will be an inner sealing surface 26 which has a stent at its distal end but on the outside surface of the inner tube 14.

FIGS. 7 to 11 show the various stages of mounting the stent graft adaptor of the present invention on to a delivery device and the delivery of that device into the vasculature of a patient. Only part of the delivery device is depicted. The delivery device includes a nose cone dilator 104 mounted on to a guide wire catheter 106 which extends from a pusher 108. The stent graft adaptor 100 in its ready to deploy condition is mounted on to the delivery device so that the distal end 26 of the inner portion of the inner tube 14c and the stent 24 is retained by a retention arrangement 110 just distal of the nose cone dilator 104. The distal end 28 of the outer tube 12 is retained to the pusher 108 by a release arrangement 112.

When the adaptor 100 has been so mounted a constraining sleeve 114 is placed around the device 100 and the sleeve extends forward to the nose cone dilator 104 as shown in FIG. 8.

Figure 9:
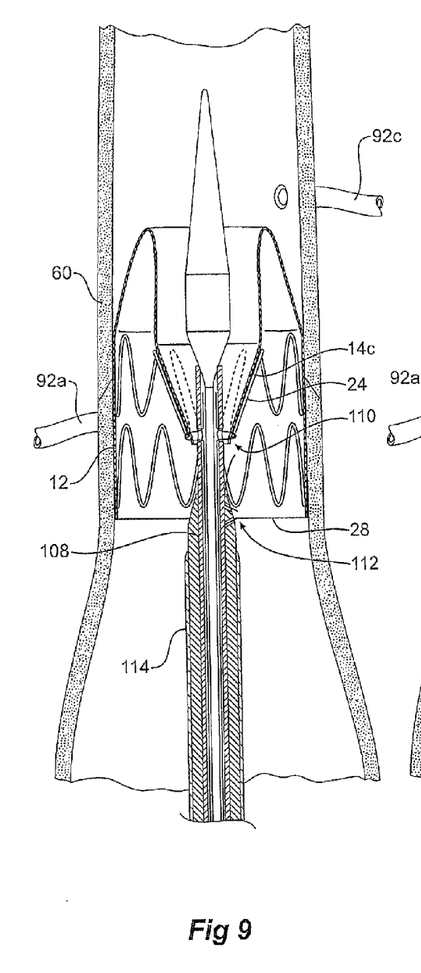
FIGS. 9 to 11 show various stages in the deployment of the device of the present invention of the embodiment shown in FIGS. 5 and 6.

As shown in FIG. 9 the introducer has been introduced into the vasculature of the patient and the sheath 114 withdrawn to release the outer tubular portion 12 so that it engages against the wall of the vasculature 60. This has occluded the intercostal artery 92a but not the intercostal artery 92c.

Still further in FIG. 9 the guide wire catheter and nose cone have been retracted with respect to the pusher 108 while the inner tubular portion 14c and stent 24 are still retained by the retention arrangement 110 and the distal end 28 is still retained by the retention arrangement 112.

Figure 10:
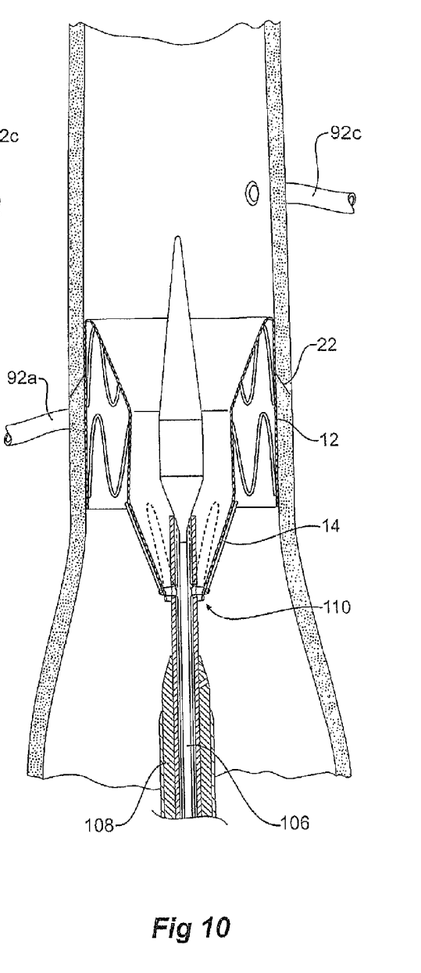

As shown in FIG. 10 the distal retention arrangement has been released so that the guide wire catheter 106 and pusher 108 can be withdrawn together so that the inner tubular portion 14 is moved down to its final position. The outer tubular portion 12 remains essentially in its same position because of the barbs 22 engaging into the wall of the aorta 60.

Figure 11:
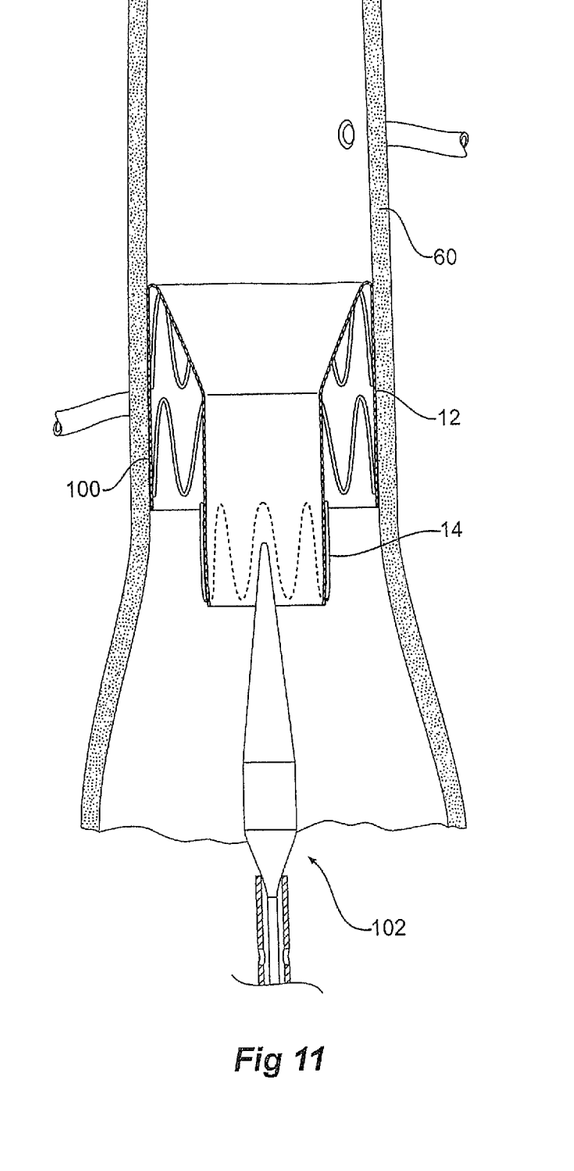

As shown in FIG. 11 the proximal retention arrangement 110 has also been released so that the stent graft adaptor 100 is completely released from the delivery device 102. The stent graft adaptor 100 is then positioned so that the outer tubular portion 12 is engaged against the wall of the aorta 60 and the inner tubular portion 14 is substantially concentric with and substantially within the outer tubular portion 12.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A stent graft adaptor comprising an outer graft tube having a first end and a second end and an inner graft tube having a first end and a second end, the outer graft tube being substantially concentric with the inner graft tube, the inner graft tube and the outer graft tube defining an annular region therebetween, the annular region having a first end and a second end, and a joining member extending between the inner graft tube and the outer graft tube, and the joining member closing off the annular region to prevent fluid flow through the annular region, the joining member comprising an annular portion of graft material that extends from a point on an inner surface of the outer graft tube intermediate the first end and the second end of the outer graft tube to a point on an outer surface of the inner graft tube intermediate the first end and the second end of the inner graft tube, and the annular portion of graft material spacing the outer graft tube apart from the inner graft tube, the second end of the outer graft tube being unconnected so that the second end of the annular region is open, wherein the inner graft tube comprises at least one self expanding stent on the outer surface thereof and the outer graft tube comprises first and second stents on the inner surface thereof, the joining member being positioned between the first and second stents.

2. The stent graft adaptor as in claim 1 wherein an outer surface of the outer graft tube comprises a sealing surface configured to engage against the wall of a vessel and the inner graft tube comprises a sealing surface to engage with a corresponding sealing surface of a stent graft deployed therethrough.

3. The stent graft adaptor as in claim 1 wherein the joining member comprises an unstented portion of graft material.

4. The stent graft adaptor as in claim 1 wherein the joining member comprises the annular portion of graft material fastened to and extending from the inner surface of the outer graft tube to and fastened to the outer surface of the inner graft tube.

5. The stent graft adaptor as in claim 1 comprising barbs extending outwards from the outer graft tube in use configured to engage with the wall of a vessel into which the stent graft adaptor is deployed.

6. The stent graft adaptor as in claim 1 wherein the outer graft tube comprises a diameter of up to 46 mm configured to fit in most descending aortas and the inner graft tube comprises a diameter of 32 mm to mate with an interference fit into a 34 mm thoracoabdominal device and the outer graft tube comprises a length of about 50 mm.

7. The stent graft adaptor as in claim 1 wherein the second end of the outer graft tube, the second end of the inner graft tube, and the second end of the annular region is a distal end of the outer graft tube, a distal end of the inner graft tube, and a distal end of the annular region, respectively.

8. The stent graft adaptor as in claim 1 having a single joining member.

9. The stent graft adaptor as in claim 1 wherein the inner graft tube, the outer graft tube, and the joining member are formed from a single piece of biocompatible graft material.

10. A stent graft adaptor comprising an outer graft tube and an inner graft tube, the outer graft tube being substantially concentric with the inner graft tube, the outer graft tube and the inner graft tube defining an annular region therebetween and a joining member extending between the inner graft tube and the outer graft tube and the joining member closing off the annular region to prevent fluid flow through the annular region and the joining member spacing the outer graft tube apart from the inner graft tube, the joining member being an unstented portion of graft material, a distal end and a proximal end of the outer graft tube being unconnected to the inner graft tube so that a distal end and a proximal end of the annular region is open, the inner graft tube comprising at least one self expanding stent on an outer surface thereof and the outer graft tube comprising at least one self expanding stent on an inner surface thereof, whereby an outer surface of the outer graft tube provides a sealing surface configured to engage against the wall of a vessel and the inner graft tube provides a sealing surface to engage with a corresponding sealing surface of a stent graft deployed therethrough.

11. The stent graft adaptor as in claim 10 comprising barbs extending outwards from the outer graft tube in use configured to engage with the wall of a vessel into which the stent graft adaptor is deployed.

12. The stent graft adaptor as in claim 10 having a single joining member.

13. The stent graft adaptor as in claim 10 wherein the inner graft tube, the outer graft tube, and the joining member are formed from a single piece of biocompatible graft material.

14. The stent graft adaptor as in claim 10 wherein the outer graft tube comprises first and second stents on an inner surface thereof, and the joining member being positioned between the first and second stents.

15. A stent graft adaptor in combination with an introducer, the introducer comprising a pusher, the pusher comprising a proximal end configured to be introduced into a patient and a distal end, a dilator at the proximal end of the pusher and a first temporary retention arrangement on the pusher distal of the dilator,
the stent graft adaptor comprising an outer graft tube and an inner graft tube, the outer graft tube being substantially concentric with the inner graft tube, the inner graft tube having a first diameter and a proximal end and a distal end, the outer graft tube having a second diameter and a proximal end and a distal end, the first diameter being smaller than the second diameter, a joining member extending between the inner graft tube and the outer graft tube, the joining member being an unstented portion of graft material, the inner graft tube comprises one self expanding stent on an outer surface thereof and the outer graft tube comprises first and second stents on an inner surface thereof, and the joining member being positioned between the first and second stents of the outer graft tube, the one self expanding stent on the inner graft tube being at a distal end of the inner graft tube,
the distal end of the outer graft tube being unconnected so that the distal end of the annular region is open,
the stent graft adaptor being mounted onto the introducer with the distal end of the inner graft tube and the one self expanding stent of the inner graft tube retained distally of the dilator by the first temporary retention arrangement and the joining member and the outer graft tube extending distally thereof.

16. The stent graft adaptor in combination with the introducer as in claim 15 further including a second temporary retention arrangement distal of the first retention arrangement, the distal end of the outer graft tube being temporarily retained by the second temporary retention arrangement.

17. The stent graft adaptor in combination with the introducer as in claim 15 comprising barbs extending outwards from the outer graft tube in use configured to engage with the wall of a vessel into which the stent graft adaptor is deployed.

18. The stent graft adaptor in combination with the introducer as in claim 15 having a single joining member.

19. The stent graft adaptor in combination with the introducer as in claim 15 wherein the inner graft tube, the outer graft tube, and the joining member are formed from a single piece of biocompatible graft material.

* * * * *